United States Patent [19]

Nishino et al.

[11] 4,276,228
[45] Jun. 30, 1981

[54] 1,6,11-UNDECANE TRIISOCYANATE

[75] Inventors: Masaki Nishino, Kawasaki; Yutaka Yasuhara, Nagoya, both of Japan

[73] Assignee: Toray Industries, Inc., Tokyo, Japan

[21] Appl. No.: 47,737

[22] Filed: Jun. 12, 1979

[30] Foreign Application Priority Data

Jun. 19, 1978 [JP] Japan ................. 53-73196

[51] Int. Cl.$^3$ .......................... C07C 119/042
[52] U.S. Cl. ................. 260/453 AL; 260/453 PH; 528/44
[58] Field of Search .............. 260/453 AL, 453 PH, 260/583 P

[56] References Cited

U.S. PATENT DOCUMENTS

| | | | |
|---|---|---|---|
| 3,218,345 | 11/1965 | Rainer | 260/453 AL |
| 3,267,122 | 8/1966 | Lehmann et al. | 260/453 AL |
| 3,412,156 | 11/1968 | Veda et al. | 260/583 P |
| 3,455,883 | 7/1969 | Ramal et al. | 260/453 AL |

FOREIGN PATENT DOCUMENTS 44-28287 11/1969 Japan .

*Primary Examiner*—Dolph H. Torrence
*Attorney, Agent, or Firm*—Miller & Prestia

[57] ABSTRACT

There is provided a novel aliphatic triisocyanate, 1,6,11-undecanetriisocyanate having the formula,

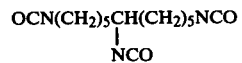

and a method for production of the same. The novel triisocyanate is produced by reacting 1,6,11-undecane-triamine or its salts with phosgene.

1 Claim, No Drawings

1,6,11-UNDECANE TRIISOCYANATE

BACKGROUND OF THE INVENTION

This invention relates to a novel aliphatic triisocyanate and a method for producing the same.

It has long been known that aliphatic isocyanates impart premium properties to urethanes derived therefrom in terms of light stability. However, a conventional aliphatic isocyanate such as hexamethylene diisocyanate is characterized by toxicity which renders its handling and use extremely hazardous.

Accordingly, they are often converted to polyisocyanates having a higher molecular weight before subjecting to a practical use in order to lower the toxicity. Such a conversion may be carried out by reacting a relatively low molecular weight polyisocyanate with various polyfunctional compounds such as polyhydroxyl compounds and biuret derivatives. Examples of those converted polyisocyanates, as derived from hexamethylene diisocyanate, are as follows:

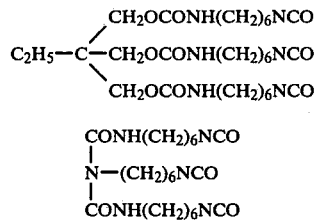

$$CONH(CH_2)_6NCO$$
$$N-(CH_2)_6NCO$$
$$CONH(CH_2)_6NCO$$

In such a conversion, however, a considerable amount of the starting isocyanates, hexamethylene diisocyanate in the above examples, tends to remain unreacted. As a result, the mixtures thus obtained are often still toxic. Such conversion processes also involve a higher production cost. The converted polyisocyanates as mentioned above are usually so viscous that they inevitably require diluents for convenient handling and use, and may be unsuitable for usage as high solid type coatings.

Therefore, it has long been desired to produce polyisocyanates that have a low toxicity and viscosity, and that can give a polyurethane resin or coatings having excellent properties with respect to light stability, water-proof, stabilities against organic and inorganic substances and so on.

It is therefore an object of the present invention to provide a novel aliphatic polyisocyanate especially suitable for preparation of a non-yellowing polyurethane. It is a further object to provide a process to produce the novel polyisocyanate from readily available raw materials in high yield by a simple process.

BRIEF SUMMARY OF THE INVENTION

We have now discovered a novel aliphatic triisocyanate, 1,6,11-undecanetriisocyanate represented by following Formula (I)

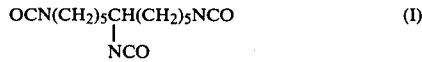

and have found that the triisocyanate has excellent properties as described below. The novel triisocyanate is produced by reacting 1,6,11-undecanetriamine, represented by the following Formula (II)

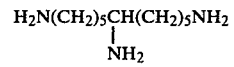

or its salts with phosgene.

DESCRIPTION OF THE SPECIFIC EMBODIMENTS

The novel triisocyanate of the present invention is produced by reacting 1,6,11-undecanetriamine or its salts with phosgene. The starting triamine can be produced by processes already known. For example, 7-(5'-aminopentyl)-3,4,5,6-tetrahydro-2H-azepine (hereinafter referred to as the "Schiff's base"), represented by the following Formula,

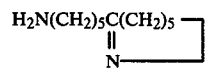

can be converted to the triamine by catalytic hydrogenation in the medium of an aqueous solution of ammonia.

The "Schiff's base" can be readily produced by thermolysis of ε-caprolactam, ε-aminocaproic acid or an oligomer or polymer thereof in the presence of a hydroxide or oxide of an alkali metal or alkali earth metal such as lithium and calcium.

The triamine thus produced is converted to the novel triisocyanate of the present invention by reacting with phosgene or other carbonyl dihalide. Phosgene may be employed in either liquid or gaseous form. The amine may be supplied to the reaction zone in the form of amine salts formed with hydrogen chloride, sulfuric acid, phosphoric acid, carbonic acid, or carboxylic acids such as acetic acid. The amine hydrochloride may be preferably employed. The amine salt is dispersed in an inert liquid reaction medium and phosgene is added thereto preferably in a stoichiometrical excess to the amino group existing in the reaction system. The temperature of the reaction medium is maintained within the range of from about 100° C. to about 230° C., preferably about 180° C. In this one step method, the amine hydrochloride or other salts are in a pulverized form having an average size of below 1 mm, more preferably below 0.3 mm, since the amine salts scarcely dissolve in the reaction mixture.

Alternatively, the phosgenation of the amine can be carried out in a multi-step method. In a preferred embodiment of the invention, the phosgenation of the amine is first carried out in an inert liquid reaction medium at a temperature below 40° C., preferably below 8° C., for a sufficient period to produce the corresponding carbamoyl chloride represented by following Formula.

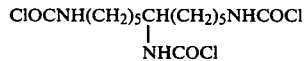

Then the reaction mixture is heated, while being stirred, to be maintained at a temperature in the range of from about 60° C. to about 230° C., preferably in the range of about 100° C. to about 180° C. in the presence of phosgene. In the first step of said phosgenation, the reaction may be carried out by adding phosgene to the amine solution in an inert medium, or preferably by adding the solution of the amine in an inert medium to liquified phosgene or phosgene dissolved in an inert medium. Also in these cases, phosgene may be preferably used in a stoichiometrical excess to the amino groups. The carbamoyl chloride thus produced is not necessarily isolated, and may be subjected to the second step of the phosgenation in situ. This two step procedure may have advantages over the one step method because the one step method tends to produce side products which result from the secondary reaction of the isocyanate with the starting amine.

In any procedure for phosgenation in the invention, the molar ratio of phosgene to the amine hydrochloride group may be from about 1.1:1 to 10:1 and preferably at least 2:1. Suitable inert liquid reaction media for the phosgenation include aromatic hydrocarbons, chlorinated aromatic hydrocarbons, chlorinated aliphatic hydrocarbons, etc. After completion of the phosgenation, the product, 1,6,11-undecanetriisocyanate may be purely isolated by distillation from the reaction medium. However, in case trace amounts of impurities which have hydrolyzable chlorine compounds are contained in the product, the distillation can to be carried out in the presence of anhydrous bases such as calcium oxide, potassium carbonate, sodium carbonate, etc, to allow recovery of the isocyanate practically which is free from the chlorine compounds.

The triisocyanate thus produced has been found to have several unusual properties, and confirmed to be a novel compound, which belongs to a new type of aliphatic triisocyanates. The triisocyanate of the present invention possesses advantages over aliphatic isocyanates of the prior art. This isocyanate differs significantly from the other aliphatic isocyanates, such as hexamethylene diisocyanate or 2'-isocyanatoethyl-6-isocyanatocaproate because of its substantially reduced toxicity and strong resistance to the action of alkaline substances. Some of these properties may be attributed to the chemical structure of the novel isocyanate as it has neither any hetero-atoms such as oxygen and nitrogen, nor any unsaturated bonds in the molecule except for the three NCO groups. The novel isocyanate of the present invention boils at 166° to 167° C. under a vacuum of 0.2 torr. This range of boiling point will be appreciated to be well-balanced from the view-point of purification and toxicity: this isocyanate generates scarcely any odor or vapor irritating to the nose, eyes, throat, etc, because of its low vapor pressure, whereas it can be easily purified by a vacuum distillation.

Moreover, the NCO group content in the novel triisocyanate of the present invention reaches as high as about 45 weight percent, based on the total weight of the triisocyanate. Furthermore, the novel triisocyanate has low viscosity so that it does not necessarily require a process to dilute it with solvents for the purpose of lowering viscosity for practical usage. Before this invention, we have not known of any aliphatic polyisocyanates possessing such high purity, low toxicity, high NCO content, and moderately low viscosity.

The novel isocyanate of the present invention may be used in the same fields as aliphatic polyisocyanates of prior art have been used. For example, it can be used in the fields such as polyurethane by reacting various compounds, including polymers, containing active hydrogen groups such as polyols, as well as intermediates for producing other novel compounds or polymers, and so on. Polyurethanes are used for paints, films, foams, elastomers, adhesives, treating agents for textiles, and so on. Especially, the employment of the novel triisocyanate for producing polyurethanes brings satisfactory advantages to the products with respect to duarability, water resistance, resistance to the acids or bases as well as organic solvents, and light-stability in comparison with that derived from available aliphatic polyisocyanates.

The following examples will serve to further illustrate the present invention.

EXAMPLE 1

In a 100 ml autoclave were placed 14 g of 7-(5'-aminopentyl)-3,4,5,6-tetrahydro-2H-azepine, 30 ml of 28% aqueous ammonia and 3 ml of Raney-Nickl. After the inside of the autoclave was flushed with hydrogen, the autoclave was pressurized with hydrogen until a pressure of 80 atm was reached, and heated it at 90° C. for 8 hrs. After the catalyst was filtered off, the water and ammonia were distilled off and the resulting residue was analysed by gas-chromatography and found to contain 13 g of 1,6,11-undecanetriamine and 1.8 g of 2-(5'-aminopentyl)-perhydroazepine. The residue was distilled at 132° C. at 2 torr to give the pure triamine.

EXAMPLE 2

To a solution of 100 g of 1,6,11-undecanetriamine obtained in Example 1 in 100 ml of methanol, 136 ml of concentrated (35 wt percent) hydrochloric acid was added drop wise while cooling to maintain the reaction temperature at below 30° C. The reaction mixture was concentrated by means of a rotary evaporator in vacuo on a hot-water bath to yield a thick oil. The oil, which on digestion with 500 ml of i-propyl alcohol was similarly concentrated, was evacuated at about 80° C. under a vacuum below 5 torr for 10 hrs to give white solids of 1,6,11-undecanetriamine trihydrochloride. The solids thus obtained were crushed and pulverized in a mortar with a pestle under a dry atmosphere to give fine powders of below 175 μm size by passing through a screen of 80 mesh.

A four-necked, round-bottomed flask fitted with a mechanical stirrer, a thermometer, a gas inlet almost reaching the bottom of the flask and a condenser was charged with 66.5 g of the powders of the triamine hydrochloride and 665 ml of o-dichlorobenzene. The mixture was phosgenated by using a phosgene flow of approximately 30 g/hr. The reaction was started at 130° C. and gradually heated to 140° C. after 4 hrs, then maintained for 7 hours at 140° C. and further for 4 hrs at 150° C. As the reaction proceeds, starting powders suspended in the mixture are disolved. After cooling to room temperature and filtration, the solvent was distilled off at about 40° C. under reduced pressure of about 4 torr and the product was distilled at 166° C. to 167° C. at 0.2 torr to give 47.2 of 1,6,11-undecane triisocyanate:

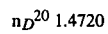

$n_D^{20}$ 1.4720

Analysis—Calc'd for $C_{14}H_{21}N_3O_3$ (percent): C 60.19; H 7.58; N 15.05, Found C 59.89; H 7.55; N 14.82.

High-resolution MS—Calc'd for $C_{14}H_{21}N_3O_3$, M+/e=279.1584, Found M+/e=279.1585.

IR Spectra (cm$^{-1}$)—2940, 2860, 2260(NCO), 1460, 1360.

NMR Spectra (ppm)—1.45(singlet, 16H), 3.4(distorted triplet, 5H).

EXAMPLE 3

In a four-necked, round-bottomed 3-liter flask on an ice-water bath, charged with 1.5 l of o-dichlorobenzene and phosgene generated by decomposing 740 g of trichloromethyl chloroformate over activated carbon, was added a solution of 300 g of 1,6,11-undecanetriamine in 200 ml of o-dichlorobenzene for 2 hrs with mechanical stirring. Then the mixture was heated to 70° C. on an oil bath and stirred while being treated with a phosgene flow at 70° C. for 30 min. The resulting mixture continued to be stirred at 130° C. for 2 hrs, at 140° C. for 2 hrs, and finally at 150° C. for 2.5 hrs, while phosgene was being blown through the mixture. After cooling the mixture and filtering it, the solvent was distilled off and the product was distilled at 189° C. at 0.6 torr to give 236 g of the crude desired isocyanate. 77 g of the crude product was distilled in the presence of 0.8 g of potassium carbonate at 168° C. at 0.2 torr to give the pure isocyanate. Alternatively, 25 g of the crude product was distilled in the presence of 0.25 g of calcium carbonate at 178°–180° C. at 0.5 torr to give 22 g of the pure isocyanate.

EXAMPLE 4

As mentioned in Example 2, into a solution of 300 g of the triamine in 300 ml methanol was added 430 ml of 36 wt percent of concentrated hydrochloric acid drop by drop for 3 hrs, while cooling below 30° C. with mechanical stirring. The mixture, being mixed with 300 ml of i-propyl alcohol, was subjected to distillation at 50°–60° C. under reduced pressure by means of a rotary evaporator. The product, being mixed with 200 ml methanol and 300 ml i-propyl alcohol, was subjected to distillation in the same manner and on repeating distillation once more the product was evacuated at 80° C. at 2 torr for 8 hrs to give white solids. The solids were pulverized and sieved by being passed through a screen of 60 mesh.

A four-necked, round-bottomed 4-liter flask was charged with 2.2 l of o-dichlorobenzene and 350 g of the triamine trihydrochloride produced above. The mixture was phosgenated for 13.5 hrs by using a flow of phosgene generated by decomposing 1.5 l of trichloromethyl chloroformate over activated carbon, while the reaction temperature being maintained at 130° C. for 3 hrs, then at 140° C. for 3.5 hrs and further at 150° C. for 7 hrs. After distillation of the solvent in the same manner as described in Example 2, 255.6 g the triisocyanate was distilled at 183°–189° C. at 0.6 torr.

EXAMPLES 5–11

Each component shown in Table 1 was mixed with the isocyanate compound. Thus resulting liquids were coated onto tin panels, and then the coated panels were cured at 120° C. for 2 hours. The resulting films had various properties and exhibited an excellent gloss.

TABLE 1

| Example | Isocyanate Compound | Polyol Component | NCO/OH (mole ratio) | Property |
|---|---|---|---|---|
| 5 | 1,6,11-Undecane triisocyanate | Trimethyrol propane | 1.0 | Hard |
| 6 | 1,6,11-Undecane triisocyanate | Glycerol | 1.0 | Hard Tough |
| 7 | 1,6,11-Undecane triisocyanate | 1,2,6-Hexanetriol | 1.0 | Hard |
| 8 | 1,6,11-Undecane triisocyanate | Polypropyleneglycol (Mn = 410) | 1.0 | Soft Elastic |
| 9 | 1,6,11-Undecane triisocyanate | Trimethyrol propane | 1.0 | Hard |
| 10 | 1,6,11-Undecane triisocyanate | Glycerol | 1.0 | Hard Tough |
| 11 | 1,6,11-Undecane triisocyanate | Polypropyleneglycol (Mn = 2000) | 1.0 | Soft Elastic |

What we claim is:

1. 1,6,11-undecane triisocyanate represented by following formula,

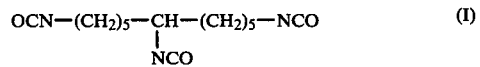

$$OCN-(CH_2)_5-\underset{\underset{NCO}{|}}{CH}-(CH_2)_5-NCO \qquad (I)$$

* * * * *

UNITED STATES PATENT AND TRADEMARK OFFICE
CERTIFICATE OF CORRECTION

PATENT NO. : 4,276,228
DATED : June 30, 1981
INVENTOR(S) : Nishino et al

It is certified that error appears in the above-identified patent and that said Letters Patent are hereby corrected as shown below:

Column 4, line 56 "47.2" should read --47.2g--

Signed and Sealed this

Twentieth Day of April 1982

[SEAL]

Attest:

GERALD J. MOSSINGHOFF

Attesting Officer    Commissioner of Patents and Trademarks